United States Patent [19]

Armstrong

[11] 4,374,644
[45] Feb. 22, 1983

[54] BLOOD CELL VOLUME MONITORING

[75] Inventor: Douglas Armstrong, Coral Springs, Fla.

[73] Assignee: Coulter Electronics, Inc., Hialeah, Fla.

[21] Appl. No.: 251,668

[22] Filed: Apr. 6, 1981

[51] Int. Cl.³ .................. G01N 27/04; G01N 33/50
[52] U.S. Cl. ................................. 436/63; 204/1 T; 324/71.4; 356/39; 436/149
[58] Field of Search .............. 23/230 B; 324/71 CP; 235/92 PC; 204/1 T, 195 B; 356/39

[56] References Cited

U.S. PATENT DOCUMENTS

| | | | |
|---|---|---|---|
| 2,656,508 | 10/1953 | Coulter | 324/71 CP |
| 3,259,842 | 7/1966 | Coulter et al. | 324/71 CP |
| 3,473,010 | 10/1969 | Bloomfield et al. | 324/71 CP X |
| 3,606,539 | 9/1971 | Polanyi et al. | 356/39 |
| 4,278,936 | 7/1981 | Shine | 324/71 CP |

OTHER PUBLICATIONS

Hempling, Acta Cytologica, vol. 21, No. 1, 1977, pp. 96–100.
Seiverd, "Hematology for Medical Technologists", Lea & Febiger, Philadelphia, 1972, pp. 349–357.
Gottfried et al., J. Lab. Clin. Med., Feb. 1974, pp. 324–333, vol. 83, No. 2.
Gear, J. Lab. Clin. Med., vol. 90, No. 5, Nov. 1977, pp. 914–928.
Haynes, Blood Cells, vol. 6, pp. 201–213, 1980.
Tatsumi et al., Poster No. 613 presented at the International Hematology Congress at Montreal, Canada, on Aug. 18–22, 1980.
Ueda et al., Poster No. 1459 presented at the International Hematology Congress at Montreal, Canada, on Aug. 18–22, 1980.

Primary Examiner—Arnold Turk
Attorney, Agent, or Firm—Gerald R. Hibnick; William A. Newton

[57] ABSTRACT

By subjecting cells, such as red blood cells, to a hypotonic solution or a solution having a lytic agent, the cells will rapidly attain a change in volume and electrical resistance parameters, which change is measured as a function of time, for example, by a Coulter Counter ® particle measuring instrument. The relationship between the change in the cell resistance or cell volume and the time of immersion in the volume changing solution provides a discriminator between a normality, different diseases, and certain inherited differences.

13 Claims, 3 Drawing Figures

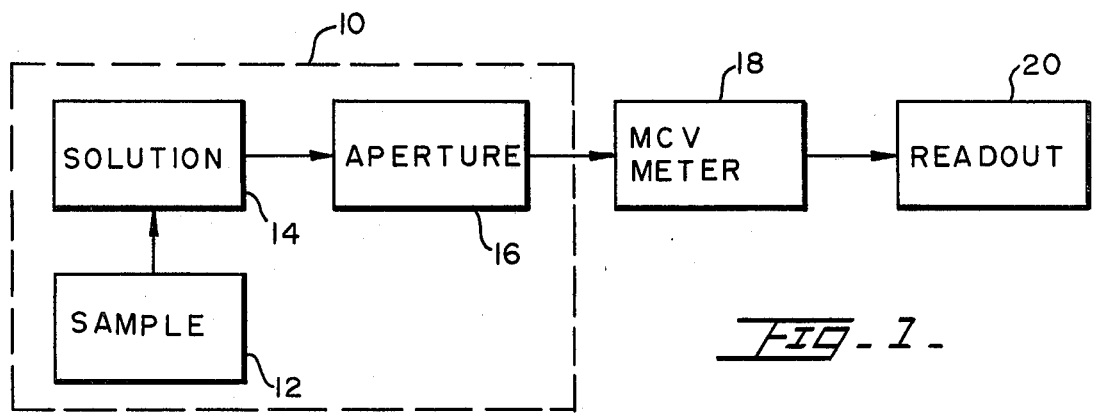
FIG-1-
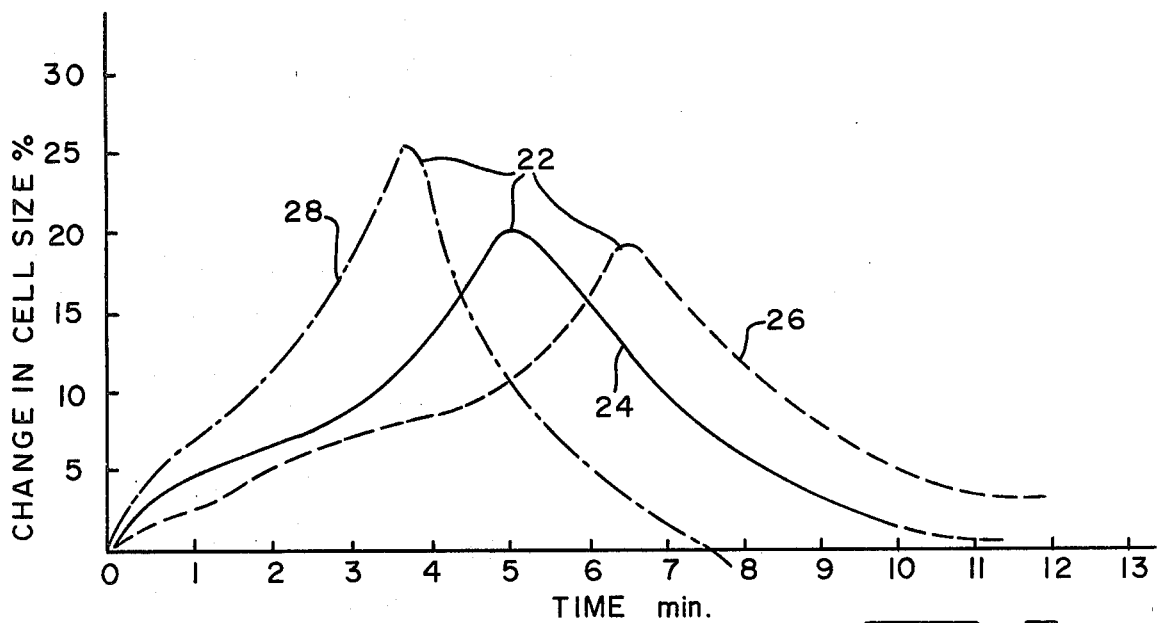
FIG-2-
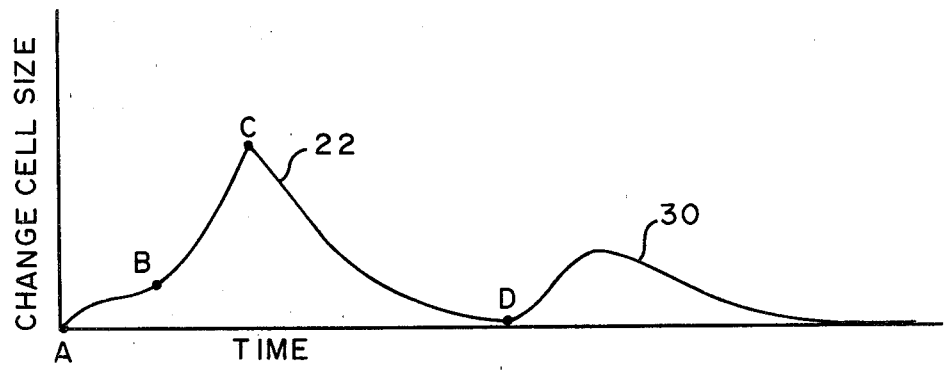
FIG-3-

BLOOD CELL VOLUME MONITORING

FIELD OF THE INVENTION

The invention pertains to a method in which the electrical resistance of biological cells, such as red blood cells, is changed by a volume changing agent. This change in electrical resistance generates a set of related data, which defines a pattern which is characteristic of the health or physiological condition of the human or animal source of the cell sample.

BACKGROUND OF THE INVENTION

The study of human cells for medical screening, diagnostic and other medical purposes is well known. For example, red blood cell count, mean cell volume (MCV), hemoglobin content and hematocrit are well known and commonly employed red blood cell parameters used in medical study and patient care.

The red blood cell is an excellent osmometer in that the cell will change in shape and volume, depending on the osmotic pressure or chemical nature of the fluid surrounding it. If the red blood cell is suspended in a solution of the same osmotic pressure as that of the intracellular fluid, the suspending fluid is said to be isotonic. Should the red blood cell be suspended in a hypotonic suspending solution, the red blood cell will swell and may even rupture due to the water taken in, in an effort to balance the internal osmotic pressure to that of the suspending solution. Other cells of the blood, namely the white blood cells and platelets, will act in much the same manner.

It is also well known that the osmotic pressure of solutions, i.e., their osmolality, such as saline solutions, varies with their concentration and types of solutes, in that the difference between the osmotic pressure within a cell and that of its suspension liquid causes the previously described change in volume and also a change in electrical resistance. In addition to a hypotonic solution, other volume changing solutions are known in the art. For instance, when red blood cells are exposed to hemolytic agents such as saponin, their membrane lipids are altered, so that water is allowed to enter the cell, causing the cell to swell and eventually rupture. If an excess of lytic agent is used, the red cell may be completely ruptured into extremely small fragments.

The above-described facts have been used extensively in the measurement of the degree of fragility of the red blood cells to changes in osmotic pressure. In several clinical disorders where the erythropoietic system is involved red blood cells demonstrate an increased or decreased fragility, depending on the specific disorder. An example of such a disorder is Thalassemia, where the cell fragility is decreased.

One apparatus of the prior art used for measuring osmotic fragility is the Fragiligraph TM sold by Manufacturer Reference. Using this apparatus, classic osmotic fragility curves have been generated by forming an increasingly hypotonic solution. A portion of the blood sample is introduced into each solution, and after a fixed time period, the degree of hemolysis is measured optically for each solution. Hemolysis is a process which is characterized by the release of the hemoglobin from the red blood cells, either by the pores of the membrane opening up or by ruptures in the membrane. From the optical measurements for each of the solutions, the percentage of hemolysis is plotted against the decreasing concentration of sodium chloride. Variations in the generated curve shapes have been recognized and related to different health conditions.

Cell and particle counting and measuring instruments, examples being those sold under the trademark Coulter Counter ® by Coulter Electronics, Inc., Hialeah, Fla., employ electronic sensing means which directly respond to the electrical resistance of each cell to count and measure each cell and progressively record cell parameters of a sample of cells in an isotonic solution. The Coulter Counter ® particle measuring instruments operate upon the well-known and documented principle of particle and cell measurement employing a sensing aperture path, which also is disclosed in Coulter U.S. Pat. No. 2,656,508 and improvement U.S. Pat. No. 3,259,842. A form of MCV measuring apparatus especially useful with a Coulter Counter ® instrument is taught in U.S. Pat. No. 3,473,010. The response of a Coulter Counter ® electric sensor is influenced at least by the shape, deformability and flow rate of the microscopic item being measured as it flows through the sensing aperture path. Since cells are subject to some deformation as they pass through the sensing aperture path, their electrical resistance measurement and their measured volume may differ from their true volume. To distinguish between true volume and measured volume, the term "apparent volume" will be employed herein to refer to measured volume. It is also well-known that as the cells swell and their pores expand, the cell will be more conductive of the current so that its apparent volume will decrease with respect to its true volume.

The above-described Coulter Counter ® has been used to study white blood cells in a hypertonic solution, as shown in the article entitled "The Permeability of the Lymphocyte Membrane: Applying a Particle Size Analyzer and a Hybrid Computer to Measure Rapid Changes in Cell Volume", by Harold G. Hempling, Acta Cytologica, Vol. 21, No. 1, 1977. A hypertonic solution has the opposite effect on the cells, in that the increase in sodium chloride over that found in a normal isotonic solution causes the cell to shrink and its volume and electrical resistance to decrease.

SUMMARY OF THE INVENTION

The invention is directed toward a method for testing cells wherein a sample of cells, each of which has an original electrical resistance, is immersed in a volume changing solution of a predetermined and fixed composition. Thereafter, the change in the cells electrical resistance is measured as a function of time, the amount of such change being dependent primarily upon the length of time of immersion and the innate and acquired properties of each cell. The measured resistance of the cells provides data which is capable of being compared to data representative of a known health or physiological condition.

BRIEF DESCRIPTION OF THE DRAWINGS

Further objects and advantages of the present invention will become apparent as the following description proceeds, taken in conjunction with the accompanying drawing in which:

FIG. 1 is a schematic of the apparatus used to practice the method embodying the invention;

FIG. 2 is a graph of a set of curves of red blood cell relative electrical resistance versus time of immersion in a volume changing solution; and FIG. 3 is a graph of a generalized curve of a blood cell relative electrical resistance versus time of immersion in a volume changing solution.

DETAILED DESCRIPTION OF THE PREFERRED EMBODIMENT

The cell osmotic activity test method embodying the invention can be carried out manually as well as semiautomatically and automatically. This test recognizes and employs the fact that cells, for example red blood cells, rapidly will change their volume and electrical resistance when immersed in a volume changing solution so as to attain a new cell volume and resistance. One such volume changing solution is a hypotonic solution, such solution being described in detail hereinafter. With a predetermined volume changing solution of fixed composition, the amount of cell change depends primarily upon the length of time the cell has been in the solution, the properties of the cell membrane and the genotype of the cell contents. Experimentation with the test method embodying the invention has verified that blood samples from normal individuals and diseased patients provide reproducible data, from which tables and curves can be obtained. The obtained data and/or curve for a given blood sample can be compared to a pre-established family of data and/or curves, each representing a different health or physiological condition. Such comparison can be used in screening and diagnostic determinations.

The test method embodying the invention can be practiced on one of the several Coulter Counter ® particle analyzing instruments, which are illustrated generally in FIG. 1 by the numeral 10. In the particle analyzer 10, a blood sample 12 is added to a volume changing solution 14, which typically is contained in a beaker. In a normal manner, the diluted blood sample is passed through a sensing aperture 16, causing a particle pulse to be generated for each cell passing therethrough. The amplitude of such particle pulse is a function of the electrical resistance of the cell, which in turn is related to the apparent volume of the cell. The detected particle pulses are fed to an MCV meter 18, which measures the apparent mean cell volume of the cells. The MCV meter 18 is of conventional design and measures MCV, for instance, over 2 second intervals, so as to print out a new MCV value every 2 seconds. A readout device 20 can be incorporated to printout the MCV for a batch or sample of blood cells. The readout device 20 can take the form of a curve plotter, for instance.

In the above-described MCV meter 18, the meter 18 allows for the continuous monitoring of the mean cell volume of the cells passing through the sensing aperture 16. It will be obvious to those skilled in the art that although it is desirable to continuously monitor the MCV readings, repeated MCV readings can be taken at short time intervals in a noncontinuous manner. Typically the readout device 20, when used to generate curves, will comprise a strip chart recorder.

For the purposes of describing the operation of the test method, the volume changing solution will comprise a hypotonic solution. The blood sample 12 is introduced into a saline solution of between 50% and 75% of normal 0.9% saline. After the blood sample is introduced, the MCV measurement produced by the MCV meter 18, will change with time. The readout device 20 can be used to record the MCV data in curves, such curves having a definite pattern. A set of sample curves are illustrated in FIG. 2, which will be described hereinafter. In general there is a time period where the cells equilibrate, then the MCV of the cells increase during a sphering or ballooning process, until a maximum MCV reading is reached, by which time at least some of the hemoglobin has been released from the cells. Thereafter, many of the cells become ghosts and the MCV reading gradually returns to the approximate range of the original MCV reading of the cells. In summary, this test method allows for measuring the change in the MCV readings of a blood sample as a function of time at particular, given osmolality system conditions that give an initial osmotic shock to the cells.

FIG. 2 illustrates osmotic activity curves which represents the output of the readout device 20 of FIG. 1, when such device takes the form of a graph-generating recorder. These curves have been generated from a blood sample of red blood cells. The variation in the MCV reading has been previously described, such MCV reading being the accumulation measurement of the resistance of several cells. With respect to the changes in resistance of an individual cell when the red blood cells experience their initial osmotic shock upon being immersed in the volume changing solution, each cell swells to increase its size and its measured resistance, so as to reach a peak size and electrical resistance measurement. Thereafter, the cell membrane becomes more conductive to the electrical current, either through the membrane becoming more porous or being ruptured, so that the resistivity measurement rapidly returns towards its original resistance, and in some cases, to lower resistances. After the cell becomes more conductive to the electrical current, the resistance will drop rapidly, even though the cell size may not decrease. These osmotically induced dynamic changes in the resistance of the cells are measured as a function of time in the curves 22. The pattern of dynamic change has a characteristic size, shape and position in a normal healthy individual and characteristic differences or abnormalities in several disease states, one example of which is set fourth in FIG. 2.

In FIG. 2, three osmotic activity curves 22 are shown, designated by the numerals 24, 26 and 28. The curves 24, 26 and 28 respectively represent a group of individuals having normal blood and a group having beta thalassemia minor and a group having hereditary spherocytosis. The abscissa scale of the graph shown in FIG. 2 represents the length of time during which the cell has been immersed into the volume changing agent, or to put it another way, the length of time since the initial osmotic shock. The ordinate scale of the graph to FIG. 2 represents the percent change of the MVC readout, with 0% of increase being at the origin.

As is illustrated by the curves 26 and 28, abnormal red blood cells will demonstrate variations in the curve pattern depending on the abnormal hemotological condition of the patient. In other words, in abnormal bloods the curves will demonstrate a rapid increase or slow increase in MCV readings with time, as compared to the curves of normal bloods. Likewise, variations in the rate of return of the MCV readings to the range of their original value can provide diagnostic information. More specifically, the curve 26 illustrates that thalassemia leads to increased resistance to osmotic activity; and therefore is representative of one abnormal blood condition where the cells are more osmotically resistant. The curve 28 illustrates that spherocytosis leads to decreased resistance to osmotic activity, and therefore is representative of one abnormal blood condition where the cells are less osmotically resistant.

A generalized osmotic activity curve is shown in FIG. 3 with four points A, B, C and D shown thereon. Those skilled in the art will recognize that there are numerous statistical ways in which the differences between curves 22 can be quantified. One illustrative set of indices, using the graph and points of FIG. 3, is as follows:

Index of Osmotic Resistance =
$$\frac{\text{Reading \% change in cell size of B–A}}{\text{Time in seconds}} \times 100$$

Index of Sphering =
$$\frac{\text{Reading \% change in cell size of C–B}}{\text{Time in seconds}} \times 100$$

Index of Ghosting =
$$\frac{\text{Reading \% change in cell size of D–C}}{\text{Time in seconds}} \times 100$$

Additionally, the time positions of points A through D, by themselves, can be of value. This is particularly true of point C, which represents the peak MCV reading.

Although a complete set of data points for either a plotting of the curves 22 or a numerical charting will be more informative, a few data points can be sufficiently informative for some medical screening and some diagnostic purposes.

It is to be appreciated that different measuring instruments, diluents, etc., could generate some shifts from the curves from the curves and data typlified in FIG. 2. Such shifts would be somewhat generally uniform for all data and curves developed by the specific test means and thus comparative data and curves would remain distinctive from one another. For instance, a change in Ph from optimum causes changes in peak amplitudes and shifts of the peak locations along the time scale. Additionally, temperature and freshness of the blood sample can cause some differences in the data obtained. In one preferred set of conditions utilized in the investigation of the present invention the following ingredients were used: sodium chloride in the amount of 1.019 grams with 17.4 milliequivalents per liter, potassium chloride in the amount of 8.125 grams with 110.5 milliequivalents per liter, distilled water to 1000 milliliters. The calculated osmolality of this hypotonic solution is 255.8 mosmols per kilogram of water. This osmolality is below the normal osmolality of a isotonic solution of sodium chloride, which is typically between 290 and 310 mosmols per kilogram of water. At this level of a hypotonic solution, the erythrocytes will swell without rupturing excessively.

The use of a hypotonic solution as the volume changing solution has been described above in detail. However, it will be obvious to those skilled in the art that other chemicals or solutions can create similar swelling to that of a hypotonic solution. For instance, the lytic agents, sometimes referred to as hemolytic agents, have been found to be usable as the volume changing solution and result in the generation of similar curves. Although there are numerous possible lytic agents known to the art, one lytic agent that has been experimentally used is quaternary ammonium compounds, eg., cetyltrimethylammonium bromide.

It has been found that the polarity of the electrical current passing through the sensing aperture can effect the shape of the generated curves. Moreover, it has been found that the reactions are inhibited when phosphate buffering is present.

Referring again to FIG. 3, the tail end of the curves start proceeding upward after reaching a valley past the point D. This upward movement of the curves occurs after all the red blood cells have been lysed and removed from producing electrical particle pulses. Hence, this portion of the curve, indicated by reference numeral 30, is representative of the swelling and eventual lysing of white blood cells. Hence, utilizing the same test procedure, the red blood cells can be first examined, with the subsequent examination of the white blood cells.

Although in the preferred embodiment a Coulter Counter ® is used wherein the electrical resistance of cells is measured to give an apparent MCV reading, optical particle analyzers can be used, such as illustrated in U.S. Pat. No. 3,710,933 to Fulwyler et al, to measure MCV. As with the electrical resistance method, cells which swell so as to become more porous or which rupture give scatter light signals which are measured as apparent MCV readings that understates their true volume.

Although particular embodiments of the invention have been shown and described herein, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A method of testing cells comprising the steps of:
   forming a mixture of at least one portion of a cell sample with a cell volume increasing solution having a predetermined, substantially unchanging composition, the cells of said cell sample each having an original volume;
   causing the cells to reside in said mixture for at least a predetermined duration during which the cells attain a change increase in their volume as compared to their original volume, the amount of said change depending upon the time of immersion of the cells in said cell volume increasing solution and the innate and acquired properties of each cell;
   measuring the change of volume of the cells as a function of time; and
   employing said measured differences in cell volume to define data which is capable of being compared with cell volume data representative of a known health or physiological condition.

2. The method according to claim 1, wherein said volume changing solution comprises a hypotonic solution.

3. The method according to claim 1, wherein said volume changing solution comprises a solution having a hemolytic agent.

4. The method according to claim 1, wherein said step of measuring obtains the apparent volumes of the cells.

5. The method according to claim 1, wherein said step of measuring obtains the apparent mean cell volume of the cells.

6. The method according to claim 1 or 5, wherein said step of measuring obtains the change in electrical resistance of the cells as a function of time.

7. The method according to claim 1 or 5, wherein said step of measuring obtains the change in optical signals of the cells as a function of time.

8. The method according to claim 1, wherein such step of measuring includes correlating a given attained mean cell volume measurement with the specific time of occurance that provides said given mean cell volume measurement.

9. The method according to claim 1, wherein said step of employing includes correlating a given mean cell volume measurement with an earlier mean cell volume measurement so as to derive the percent of change relative to the said earlier mean cell volume measurement.

10. The method according to claim 1, wherein said step of employing includes forming a curve plotted from said defined set of data.

11. The method of claim 1, wherein the step of measuring comprises monitoring the mean cell volume continuously.

12. The method according to claim 1, wherein the step of measuring comprises making repeated mean cell volume measurements on the blood sample at appropriate time intervals.

13. The method of claim 1, wherein said predetermined duration is of sufficient length to allow lysing of the white cells, the method including the further step of, after measuring the change in electrical resistance of red blood cells, measuring the change in electrical resistance of white blood cells during the same operational run.

* * * * *